(12) United States Patent
Keane et al.

(10) Patent No.: US 7,351,228 B2
(45) Date of Patent: Apr. 1, 2008

(54) PLUNGER ROD FOR ARTERIAL BLOOD COLLECTION SYRINGES

(75) Inventors: Paul Keane, Plymouth (GB); Paul Barkell, Plymouth (GB)

(73) Assignee: Becton, Dickinson and Company, Franklin Lakes, NJ (US)

( * ) Notice: Subject to any disclaimer, the term of this patent is extended or adjusted under 35 U.S.C. 154(b) by 695 days.

(21) Appl. No.: 10/703,197

(22) Filed: Nov. 6, 2003

(65) Prior Publication Data

US 2005/0101920 A1    May 12, 2005

(51) Int. Cl.
  *A61M 5/315* (2006.01)
  *A61M 37/00* (2006.01)
  *A61M 1/00* (2006.01)
  *A61B 5/00* (2006.01)
  *B65D 81/00* (2006.01)

(52) U.S. Cl. ............. 604/218; 604/126; 604/6.16; 600/576

(58) Field of Classification Search ........... 604/218, 604/126, 173, 181, 187, 190, 236, 238, 6.15, 604/6.16; 600/576, 573
  See application file for complete search history.

(56) References Cited

U.S. PATENT DOCUMENTS

| | | | |
|---|---|---|---|
| 4,257,426 A | 3/1981 | Bailey | |
| 4,326,540 A | 4/1982 | Bailey et al. | |
| 4,361,155 A | 11/1982 | Anastasio | |
| 4,424,817 A * | 1/1984 | Williams | 600/579 |
| 4,466,446 A | 8/1984 | Baidwan et al. | |
| 4,519,402 A | 5/1985 | Andersen | |
| 4,572,210 A | 2/1986 | McKinnon | |
| 4,595,021 A | 6/1986 | Shimizu et al. | |
| 4,617,941 A | 10/1986 | Ichikawa et al. | |
| 4,657,028 A | 4/1987 | Rich et al. | |
| 4,774,963 A | 10/1988 | Ichikawa et al. | |
| 4,821,738 A * | 4/1989 | Iwasaki et al. | 600/578 |
| 4,961,432 A * | 10/1990 | Guirguis | 600/573 |

(Continued)

FOREIGN PATENT DOCUMENTS

EP    1199104 A2    4/2002

(Continued)

OTHER PUBLICATIONS

Micro ABG Product Literature, Vital Sign Inc., 2001.

(Continued)

*Primary Examiner*—Matthew F. DeSanto
(74) *Attorney, Agent, or Firm*—Mark Lindsey (57) ABSTRACT

An arterial blood collection device is provided having a one-piece plunger rod for use with a blood collection syringe. The plunger rod is hollow, with a closed front end. A self-sealing filter is provided within the closed front end of the plunger rod. Vents are spaced radially about the front end of the plunger rod for fluid communication into the hollow interior thereof. The plunger rod is intended for use in slidable communication within a syringe barrel. In use, the plunger can be retracted within the syringe barrel to form a cavity therein. Upon arterial blood contact, the cavity fills with blood and air can be expelled from the cavity through the vents and the filter and out to ambient air. The plunger rod is a one-piece assembly, eliminating the need for a separate rubber plunger seal.

24 Claims, 7 Drawing Sheets

U.S. PATENT DOCUMENTS

| | | |
|---|---|---|
| 5,181,523 A | 1/1993 | Wendelborn |
| 5,314,416 A | 5/1994 | Lewis et al. |
| 5,377,689 A | 1/1995 | Mercereau |
| 5,529,738 A | 6/1996 | Mercereau |
| 5,670,097 A | 9/1997 | Duan et al. |

FOREIGN PATENT DOCUMENTS

| | | |
|---|---|---|
| EP | 1287784 A1 | 3/2003 |
| WO | WO 01/12746 A1 | 2/2001 |

OTHER PUBLICATIONS

PICO 70 Optimized Design for Arterial Blood Sampling Product Literature, Radiometer Co., date unknown.

PICO 70 Self-Filling Sampler Designed to Optimize . . . Product Literature, Radiometer Co., date unknown.

* cited by examiner

FIG. 9

PLUNGER ROD FOR ARTERIAL BLOOD COLLECTION SYRINGES

BACKGROUND OF THE INVENTION

1. Field of the Invention

The present invention relates to arterial blood collection syringes. More particularly, the present invention relates to a one-piece plunger rod for efficient use of an arterial blood collection syringe.

2. Description of Related Art

Arterial blood collection syringes are used for withdrawing and collecting arterial blood samples from the body of a patient. Once the blood sample is collected, it is subjected to diagnostic analysis for gases, electrolytes, metabolites, and other elements that are indicative of a condition of a patient. Various types of syringes have been devised for collecting arterial blood samples, which mainly comprise elements from a hypodermic syringe, i.e., a plastic or glass syringe barrel, a sealing elastomeric stopper, and a plunger rod. Additionally, certain arterial blood collection syringes include a self-sealing filter that allows passage of air out of the syringe during blood collection, while still preventing the passage of blood. This latter type of syringe having a filter allows for an anaerobic arterial sample to be collected without the need to aspirate the syringe, as is required with a syringe having a plunger rod and a plunger stopper.

Typical arterial blood collection syringes include a two-piece plunger rod assembly comprised of an elastomeric sealing stopper attached to a plunger rod. The sealing stopper and plunger rod must be assembled together in a separate operation prior to assembly with a syringe barrel. In addition, a silicone lubricant is usually used on the interior wall of the syringe barrel to facilitate easy slidable movement of the elastomeric sealing stopper against the interior wall of the syringe barrel. Such syringes typically involve an active step for obtaining a blood sample. For example, a needle connected to such a syringe accesses a patient's blood vessel, and the syringe is thereafter aspirated by drawing the plunger rearwardly within the syringe barrel so as to draw a blood sample into the syringe barrel for analysis. U.S. Pat. No. 5,314,416 to Lewis et al. discloses a low friction syringe assembly having a typical two-piece plunger rod and a plunger tip assembly.

Arterial blood samples can also be obtained passively through the use of a syringe having a plunger with a porous filter to collect blood by way of the blood pressure of a patient from whom the blood is being collected. In such a syringe, the plunger mechanism is typically hollow, and includes a porous filter therein. A separate elastomeric sealing stopper is typically attached to the front end of the plunger mechanism for sealing within the syringe barrel, with air channels in the stopper for air passage through the filter. In use, the plunger is set at a certain position against a graduated scale of the syringe barrel, so that the desired volume of the sample to be collected is represented by the cavity within the syringe. Once a blood vessel of a patient is accessed by an appropriate needle attached to the syringe, arterial blood will fill the syringe under its own pressure. As the cavity within the syringe fills, air within the syringe is allowed to escape from the syringe by way of a gas permeable filter. When the blood sample contacts the filter, the filter seals, thereby preventing escape of blood and ingress of air and other contaminants into the collected sample. U.S. Pat. No. 4,821,738 to Iwasaki et al. discloses an arterial blood gas syringe including a typical two-piece assembly for use. The arterial blood gas syringe is comprised of a plunger rod and an elastomeric sealing plug having channels formed in an upper surface for use in removing air as arterial blood is received in the syringe. The channels extend in a generally radial direction and converge near the center of a sealing plug to allow the passage of air to and through a filter element contained within the sealing plug. U.S. Pat. Nos. 5,377,689 and 5,529,738, both to Mercereau, disclose a sampling syringe including a plunger cap having an air permeable filter attached to a plunger rod, which is in slidable communication with the inner wall of a syringe barrel.

The separate rubber sealing stopper on the plunger in such assemblies provides an effective seal to contain the blood sample within the syringe. However, while such syringe assemblies are useful, the separate rubber sealing stopper typically requires a silicone lubricant for sliding movement within the syringe barrel, and further requires costly manufacturing and assembly steps. Accordingly, there is a present need for an arterial blood collection syringe which is inexpensive to manufacture and easy to assemble, and which is simple to operate.

SUMMARY OF THE INVENTION

Generally, the present invention is directed to an arterial blood collection syringe including a one-piece plunger rod assembly having an integrally molded sealing mechanism, all comprised of a single material, which is easy to manufacture and is simple to operate, with or without a silicone lubricant. The invention is an improvement over the prior art as it reduces the manufacturing costs of assembly because the plunger rod can be molded as a single part, from a common material, thereby eliminating the cost of manufacturing a separate rubber sealing stopper. The invention is a further improvement over the prior art because it eliminates the need for assembling the sealing stopper with a plunger rod in a separate assembly step. The invention is an even further improvement over the prior art because it eliminates the need for use of a silicone lubricant on the interior wall of the syringe barrel, which is traditionally used to lubricate the sealing stopper and allow smooth movement of the plunger through the syringe. Silicone oils, when used as a plunger lubricant, may enter the blood analyzer during testing of a sample within a syringe and cause contamination of the surface of the sensitive electrodes within the analyzer. The combination of a lubricating additive with the plunger rod raw material during the injection molding process may eliminate the need for silicone oils as lubricants within the syringe barrel.

The plunger rod of the present invention includes an elongated, hollow cylindrical rod comprising a rigid tubular wall defining an internal lumen and extending between an open rear end and a non-elastomeric, rigid closed front end. The front end is desirably a tapered front end having a conical profile. The plunger rod includes a plurality of vents extending through the rigid tubular wall adjacent the front end of the rod and in fluid communication with the internal lumen. Desirably, the plurality of vents extend through the rigid tubular wall at an intersection of the closed front end with the rigid tubular wall, thereby forming the vents about the perimeter of the front end. Alternatively, the plurality of vents can be equally radially spaced about the circumference of the rigid tubular wall, and extend through the rigid tubular wall at a location axially spaced from the closed front end of the rod.

The plunger rod assembly further includes a porous filter member maintained within the internal lumen at the front end of the plunger rod and adjacent the plurality of vents. The porous filter member is desirably adapted to filter fluid passing between the plurality of vents and the internal lumen of the rod. The porous filter member desirably contacts an interior surface of the closed front end within the internal lumen such that the plurality of vents are adjacent the porous filter member at a location spaced from a front surface of the porous filter member. The porous filter member is desirably constructed of a matrix which is pervious to air, and which is capable of becoming impervious to air and blood after being contacted with a blood sample.

The plunger rod may further include at least one sealing ring extending circumferentially about an external surface thereof. Preferably, the sealing ring is integrally formed with the plunger rod or, alternatively, is comprised of an elastomeric o-ring affixed to an external surface of the rod.

In a further embodiment, the invention is directed to a syringe assembly which includes such a plunger rod in combination with a syringe barrel. The syringe barrel includes a barrel having an internal chamber extending between an open rear end and a closed front end having an opening extending therethrough. At the front end, the syringe barrel includes structure for connecting the syringe assembly with a medical device, such as a needle assembly.

DETAILED DESCRIPTION OF THE INVENTION

Figure 1:
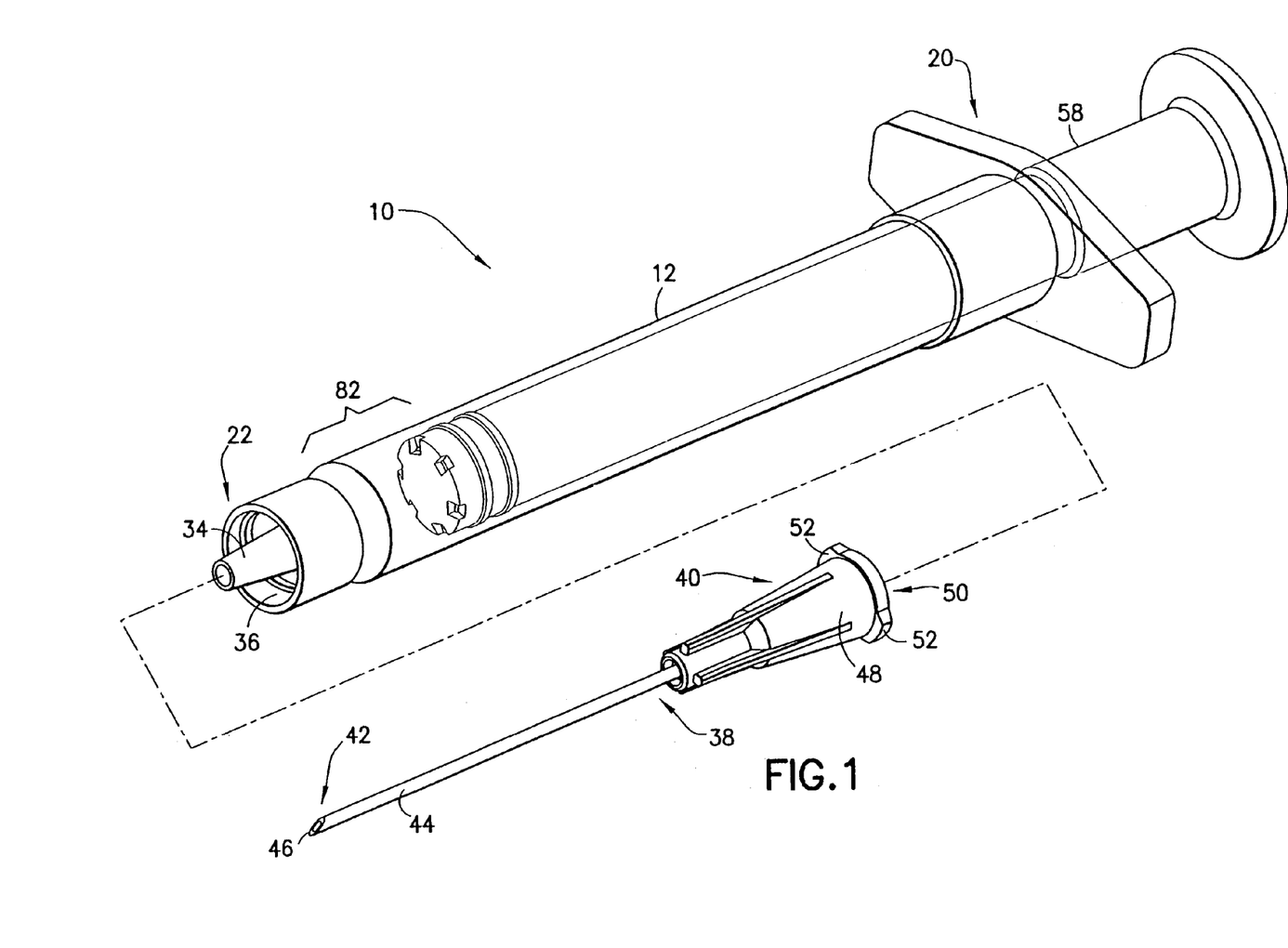
FIG. 1 is a perspective view of a plunger rod within a syringe barrel in accordance with the present invention.

Referring to the drawings in which like reference characters refer to like parts throughout the several views thereof, FIG. 1 illustrates an arterial blood collection syringe assembly 10 comprised of a plunger rod 58 in slidable communication with a syringe barrel 12 having a standard luer fitting 34 at the closed front end 22 for connection to an arterial access device, such as a needle assembly 38. The present invention is generally described in terms of an arterial blood collection syringe assembly 10. While described herein in terms of a preferred embodiment of an arterial blood collection syringe assembly 10 intended for use with a needle assembly 38, the syringe assembly 10 of the present invention may be used with or may incorporate other medical devices, such as another medical device assembly that includes a piercing element or allows for attachment to a catheter.

As shown in FIG. 1, the two primary components of the arterial blood-collection syringe assembly 10 include a plunger rod 58 in slidable communication with a syringe barrel 12. Syringe barrel 12 may be constructed of any suitable material such as glass or plastic, and is of a suitable size for collection of blood or other fluid samples.

Figure 2A:
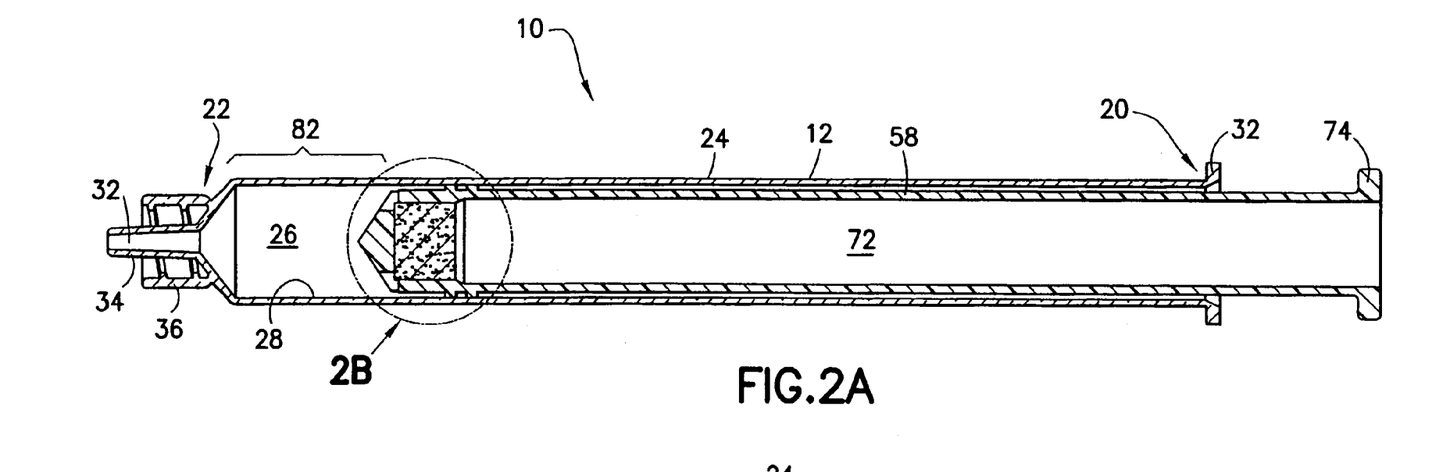
FIG. 2A is a longitudinal cross-section of the plunger rod within a syringe barrel as shown in FIG. 1.

A particular embodiment of syringe barrel 12 is shown in detail in FIGS. 1 and 2A and includes an elongated, hollow, cylindrically-shaped tube having an open rear end 20 and a generally closed front end 22. The cylindrically-shaped tube of syringe barrel 12 comprises a rigid tubular wall 24 that defines an internal space extending between open rear end 20 and front end 22. The rigid tubular wall 24 of syringe barrel 12 defines an internal surface 28 for slidably receiving the plunger rod 58. A flange 32 is provided at the open rear end 20 of syringe barrel 12 for manipulation of the arterial blood collection syringe assembly 10.

Front end 22 of syringe barrel 12 is generally closed-ended with an opening 32 extending therethrough. Front end 22 includes a fitting for attachment with an appropriate arterial access device such as a needle. For example, a standard luer fitting including a male luer taper 34 and an internally threaded luer lock 36 may be provided at front end 22 of syringe barrel 12, for removeably receiving a corresponding fitting of an arterial access device. More particularly, an arterial access device such as a needle assembly 38 as shown in FIG. 1 may include a rearward end 40 and a forward end 42. The forward end defines a needle cannula 44 beveled at the forward end 42 to define a sharp puncture tip 46 for intravenous puncture into the blood vessel of a patient, such as an artery. Puncture tip 46 is designed to provide ease in insertion and minimal discomfort for the patient during arterial access. The rearward end 40 of the needle assembly 38 includes a hub fitting 48, which includes an internal female luer taper 50 and a pair of opposing flanges 52. In this manner, needle assembly 38 can be releasably attached to the front end 22 of syringe barrel 12 by the corresponding interfitting engagement between male luer taper 34 and female luer taper 50, as well as through the locking engagement between luer flanges 52 and luer lock 36, as is well known in the art. As such, fluid communication can be established between the interior lumen of needle cannula 44 and the internal space 26 of collection assembly 10.

Figure 4:
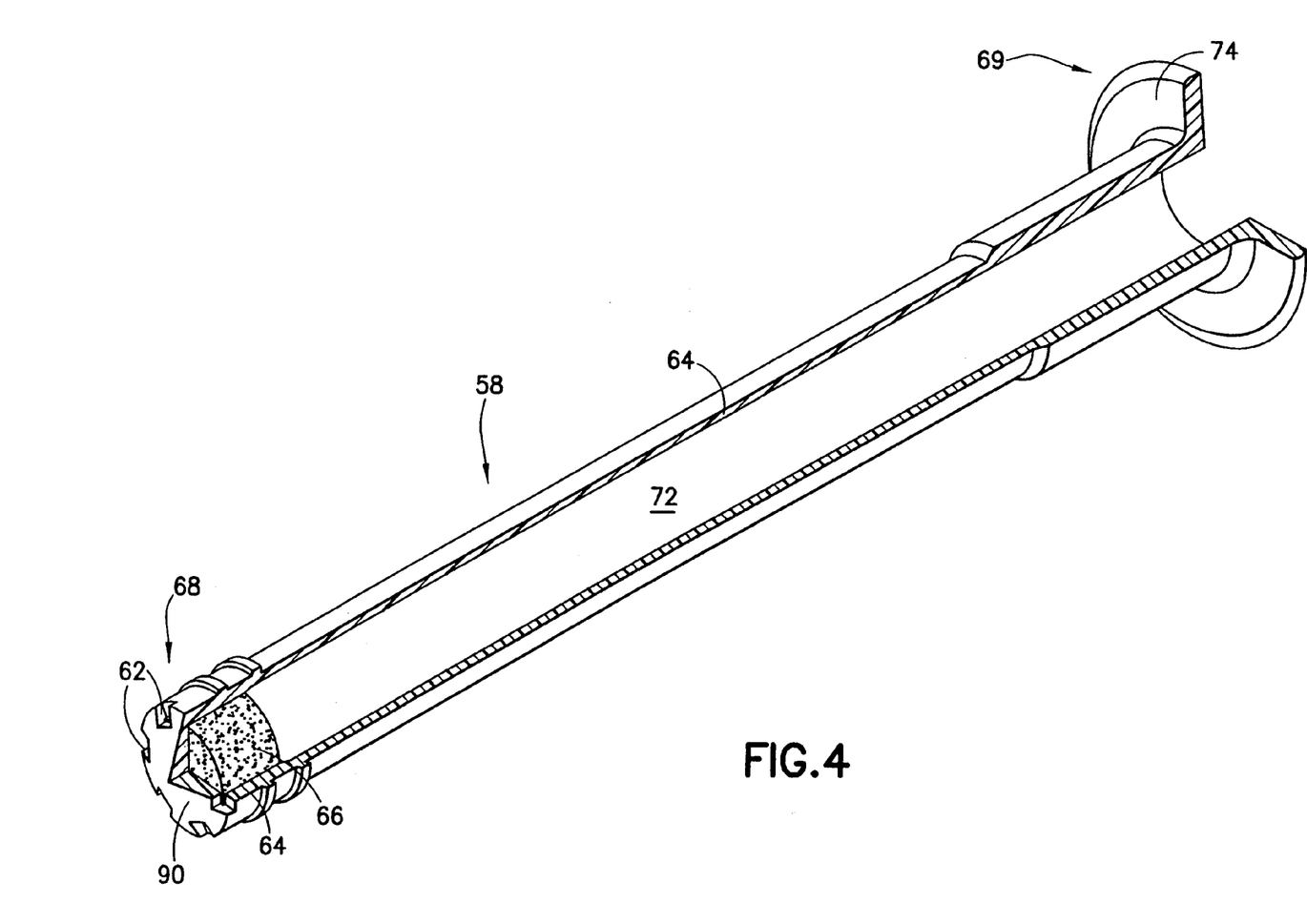
FIG. 4 is a partial sectional view of the plunger rod as shown in FIG. 3.

The arterial blood collection assembly 10 of the present invention further includes plunger rod 58 slidably received within the internal space 26 defined by tubular wall 24 of syringe barrel 12. The particular features of plunger rod 58 are shown in detail throughout FIGS. 4-6. Plunger rod 58 generally includes an elongated, hollow, cylindrically-shaped rod as shown in the sectional view of FIG. 4. The plunger rod 58 comprises a rigid tubular wall 64 extending between a closed front end 68 and an open rear end 69 establishing therein an interior lumen 72 as shown in FIG. 4. The plunger rod 58 has a circular cross-section with an external diameter that is slightly smaller than the internal diameter 28 of the syringe barrel 12. In a preferred embodiment, the closed front end 68 of plunger rod 58 includes a conical profile 90. Plunger rod 58 is desirably constructed of a suitable polymeric material, and may be manufactured by injection molding with a suitable polymer material known in the art. The plunger rod 58 may further include a flange 74 extending about the perimeter of the open rear end 69 of the plunger rod 58, which provides a means or mechanism to manipulate and axially displace the plunger rod 58 relative to the syringe barrel 12.

The plunger rod 58 further includes at least one vent, and preferably a plurality of vents 62 extending through the rigid tubular wall 64 of the plunger rod 58 at a location adjacent front end 68 thereof. Vents 62 are desirably spaced equally and radially about a circumference or perimeter of the front end 68 of the plunger rod 58 as illustrated generally in FIGS. 3-5. In a preferred embodiment, the plurality of vents 62 are positioned about the closed front end 68 of the plunger rod 58 at the intersection between the conical-profiled, closed front end 90 and the rigid tubular wall 64 of the plunger rod 58. The plurality of vents 62 extend through the rigid tubular wall 64 of the plunger rod 58, thereby providing fluid communication into the interior lumen 72 created by the rigid tubular wall 64 of the plunger rod 58.

Figure 7:
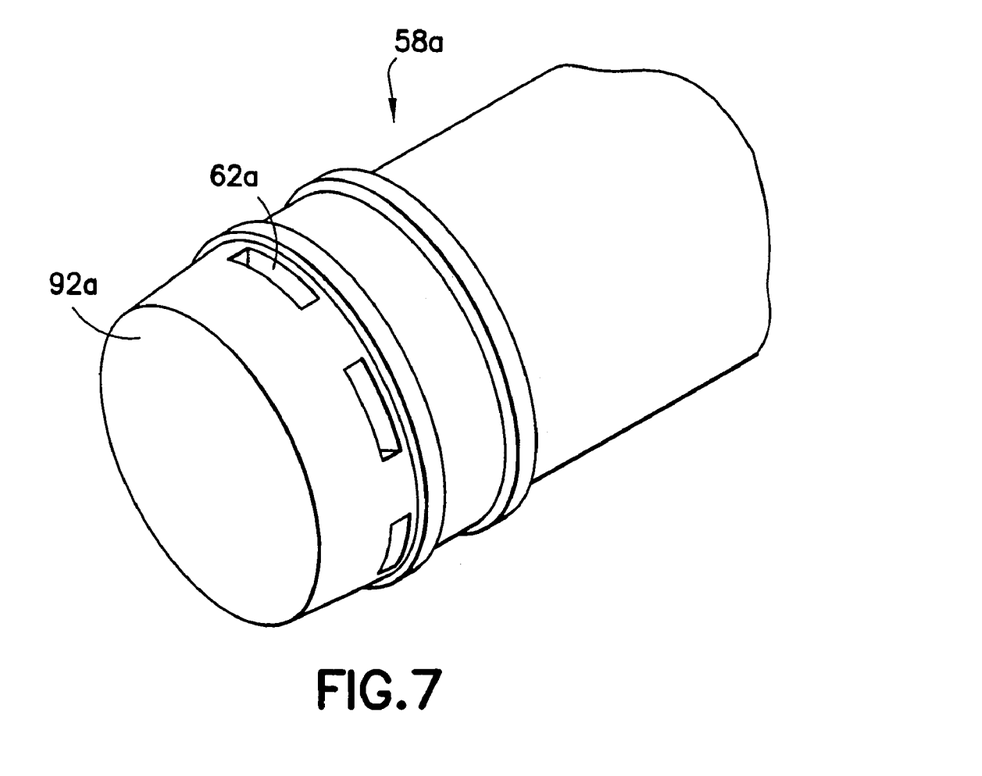
FIG. 7 is an enlarged, perspective view of the front end of a further embodiment of a plunger rod having vents radially positioned in the tubular side wall of the plunger rod.
Figure 8:
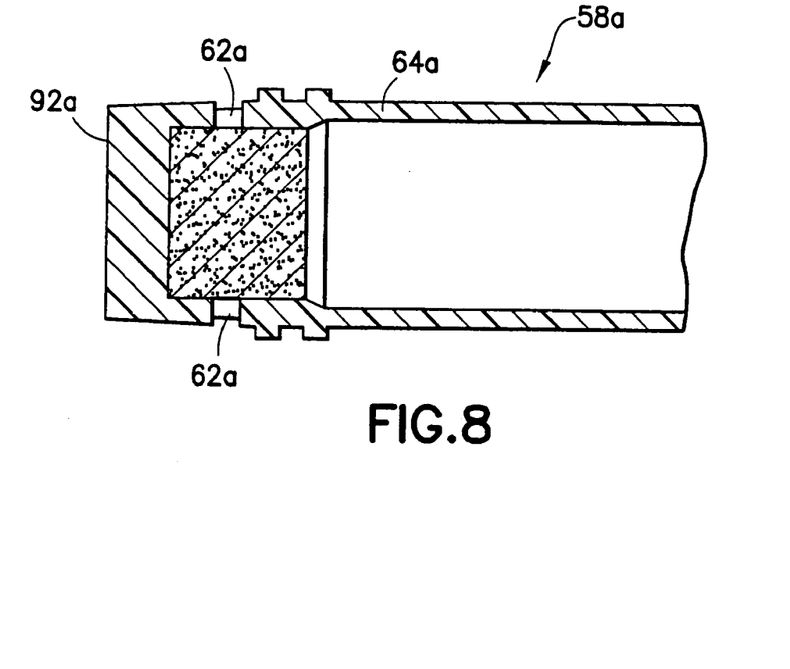
FIG. 8 is an enlarged, sectional view of the front end of the plunger rod as shown in FIG. 7.

In an alternate embodiment as shown in FIGS. 7 and 8, the plurality of vents 62*a* are equally-positioned circumferentially in the rigid tubular wall 64*a* of the plunger rod 58*a* at a location spaced from the front end. In this embodiment, the plunger rod 58*a* is also shown as including a flat profiled front end 92*a*, with the plurality of vents 62*a* positioned in the rigid tubular wall 64*a* of the plunger rod 58*a*. Such positioning of the vents spaced from the first end is possible in the plunger rod due to the sealing mechanism between the plunger and the syringe barrel being located a position spaced from the front end of the plunger rod, as compared with typical prior art assemblies. It is contemplated that in any embodiments of the invention, the front end of the plunger rod can include such a flat profiled front end, or a conical profiled front end as described in connection with FIGS. 3-5.

Figure 5:
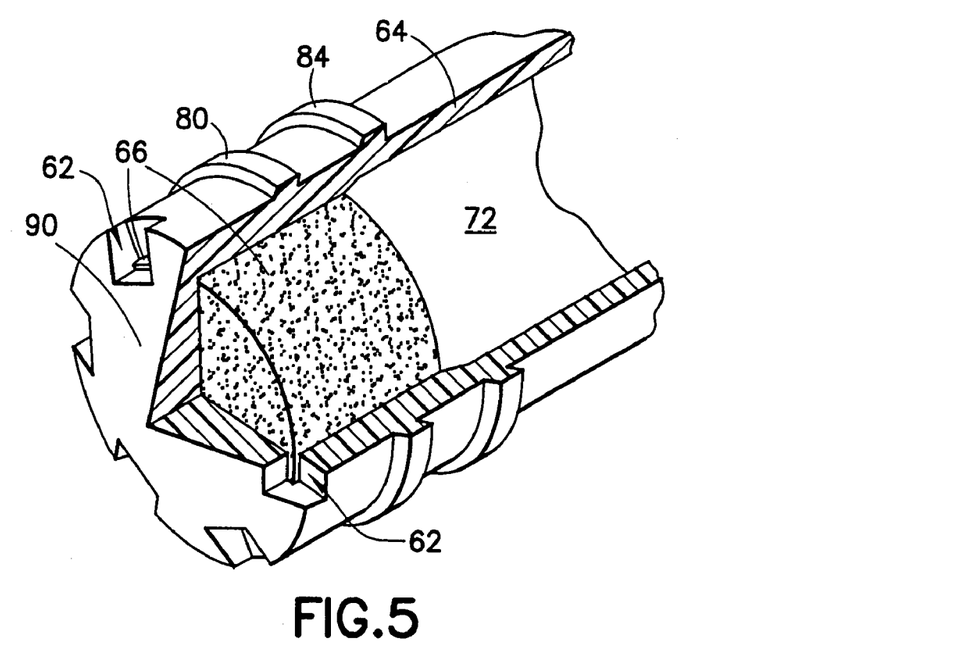
FIG. 5 is an enlarged, partial sectional view of the front end of the plunger rod as shown in FIG. 4.
Figure 6:
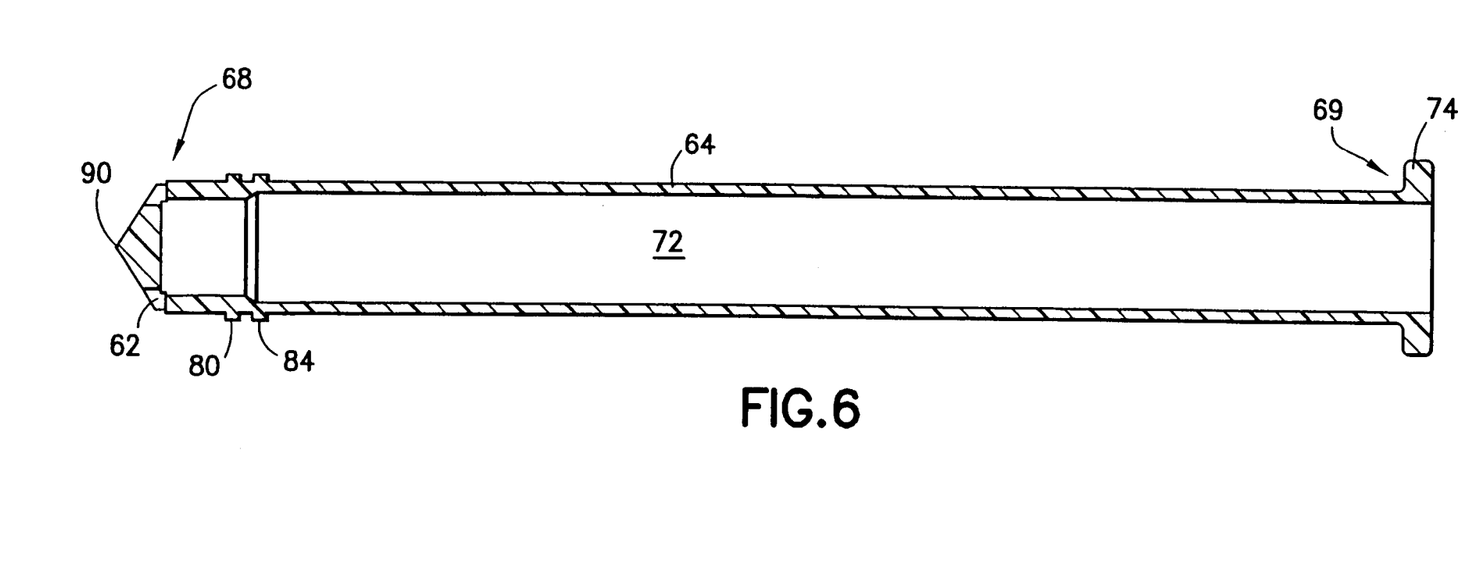
FIG. 6 is a longitudinal section of the plunger rod assembly as shown in FIG. 4.

A porous filter member 66 is housed within the interior lumen 72 of the plunger rod 58 as illustrated by FIGS. 4-6. The porous filter member 66 is located within the interior lumen 72 at a position toward the front end 68 thereof, and is desirably positioned fully within the interior lumen 72 and contacting the inner surface of the front end 68 within interior lumen 72. The porous filter member 66 is positioned so as to be in fluid communication with the plurality of vents 62. The porous filter member 66 permits air and other gases to flow from within internal space 26 of syringe barrel 12 through the vents 62 and through the interior lumen 72 out to the external environment, as will be described in more detail herein. Desirably, the porous filter member 66 is positioned within the interior lumen 72 of the plunger rod 58 by insertion of the porous filter member 66 through the open rear end 69 of the plunger rod 58 and sliding the porous filter member 66 up to the closed front end 68 of the interior lumen 72, so that an interference fit is formed between the two components.

The porous filter member 66 is constructed of a material which is permeable to gases, such as air, but is desirably impermeable to liquids, such as blood. Porous filter member 66 may be a one-way vent, in which air flows only in one direction, or more desirably may be a two-way vent, in which air is able to flow in both directions. While the porous filter member 66 permits air and gas to flow therethrough, it acts as a barrier for liquid flow in either direction. Also, once a liquid specimen such as blood contacts and/or saturates the porous filter member 66, the vent will seal to any further gas flow therethrough. As such, no air will be able to flow in or out of the vent, even once the liquid specimen has been removed.

Porous filter member 66 may be made out of any suitable material which is permeable to gases (in particular air) and impermeable to liquids (in particular blood). For example, the porous filter member 66 may be manufactured from a sintered polymer matrix with a self-sealing additive. Alternatively, any other type of porous filter member suitable for self-sealing in connection with exposure to blood or other fluid that is known in the art may also be used as the porous filter member. These types of self-sealing filters are commonly used in arterial blood collection syringes and in many other applications. Non-limiting examples of useful materials include carboxymethyl cellulose, high density polyethylene, high density polypropylene, and the like.

Figure 2B:
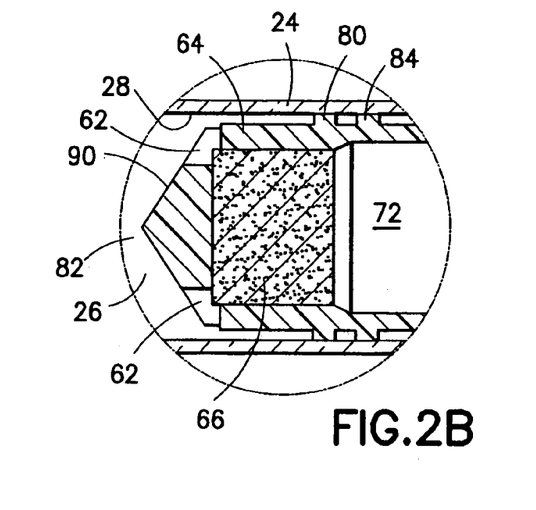
FIG. 2B is an enlarged view of the cross-section of the front end of the plunger rod showing the filter therein as shown in FIG. 2A.
Figure 3:
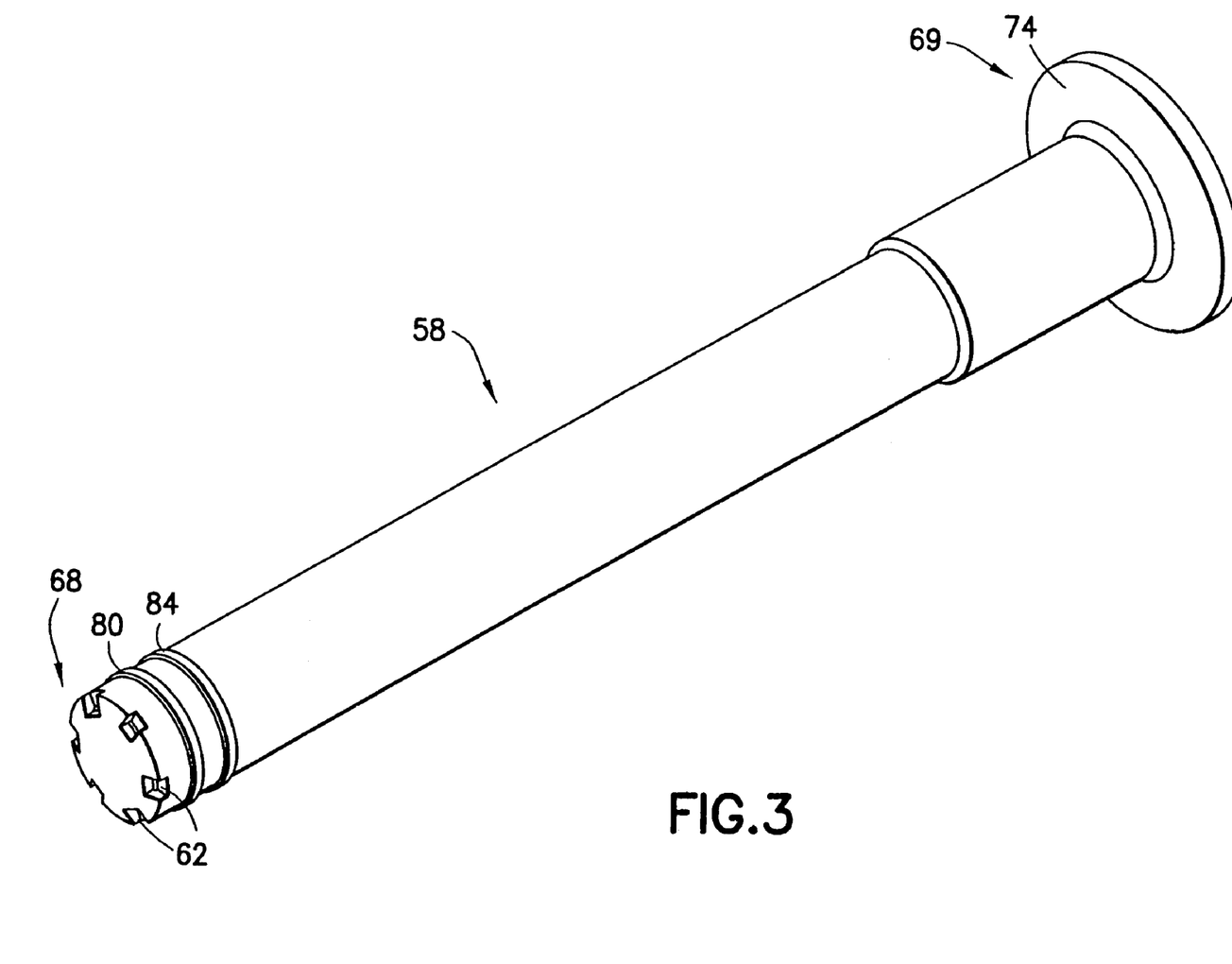
FIG. 3 is a perspective view of the plunger rod.

The plunger rod 58 further includes at least one, and more desirably two sealing rings 80, 84 extending circumferentially about the external surface of rigid tubular wall 64, as best depicted in FIGS. 3-5. Sealing rings 80, 84 are positioned circumferentially near the closed front end 68 of the plunger rod 58 at a position between the plurality of vents 62 and the open rear end 69. Sealing rings 80, 84 may be seperately attached to plunger rod 58, or more desirably are integrally molded into the exterior surface of the rigid tubular wall 64 of the plunger rod 58. The sealing rings 80, 84 are of a diameter approximately equal to or only slightly smaller than that internal diameter 28 of the syringe barrel 12 as shown in FIGS. 2A and 2B. The sealing rings 80, 84 of the plunger rod 58 slidably contact the internal surface 28 of the syringe barrel 12 and provide a fluid-tight seal between the plunger rod 58 and the internal surface 28 of the syringe barrel 12 so that a sample can be held within the cavity 82 formed within the internal space 26 between front end 22 of syringe barrel 12 and closed front end 68 of plunger rod 58, thereby preventing the sample from leaking from the syringe assembly 10. The first sealing ring 80 nearest to the closed front end 68 of the plunger rod 58 creates a primary seal between the cavity 82 formed between the plunger rod 58 and the syringe barrel 12. The second sealing ring 84 provides a secondary seal and assists in the stabilization of the plunger rod 58, thereby centralizing the plunger rod 58 during slidable movement of the plunger rod 58 relative to the syringe barrel 12.

A lubricating additive may be incorporated into the plunger rod 58 during molding thereof to assist the slidable movement of the plunger rod 58 relative to the syringe barrel 12. Such a lubricating additive eliminates the need for silicone lubricants within the syringe barrel 12, thereby preventing sample contamination and entry of such silicone lubricants into instrumentation used for sample analysis.

Figure 9:
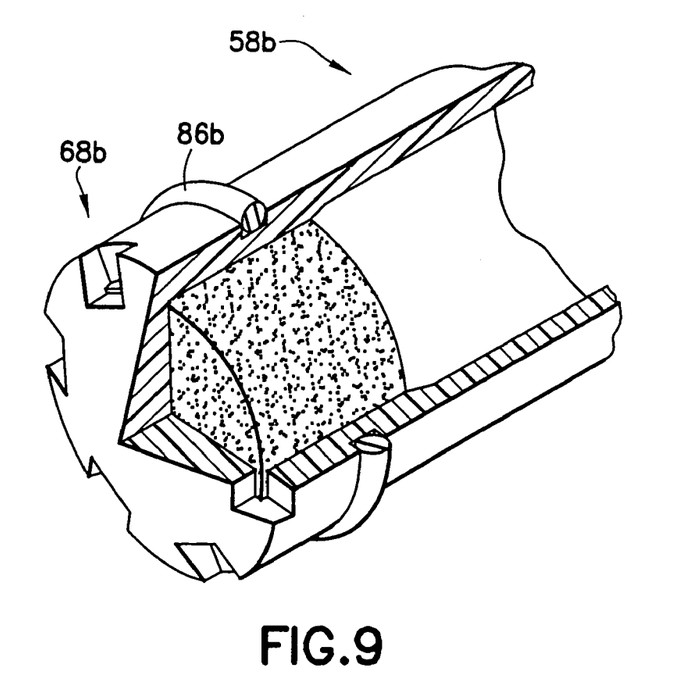
FIG. 9 is an enlarged, perspective view of a further embodiment of a plunger rod having an o-ring.

In an alternative embodiment shown in FIG. 9, the plunger rod 58*b* may include an o-ring seal 86*b* positioned on the outer diameter of the closed front end 68*b* of the plunger rod 58*b*. Such an o-ring seal is desirably constructed of an elastomeric material, such as rubber or the like. The o-ring seal 86*b* is of a diameter equal to or greater than the internal diameter of the syringe barrel, thereby providing the formation of a liquid-tight seal while relying on the resistance between the o-ring seal 86*b* and the internal surface of the rigid tubular wall of the syringe barrel. The o-ring seal 86*b* is in slidable communication with the internal surface of the syringe barrel.

Assembly of the arterial blood collection assembly 10 is accomplished by inserting the porous filter member 66 within the interior lumen 72 of the plunger rod 58 through the open rear end 69 of the plunger rod 58 and forcing the porous filter member 66 up to the closed front end 68 of the interior lumen 72, so that an interference fit is formed between the two components. The plunger rod 58 having the porous filter member 66 fixed therein can then be slidably inserted into the interior space 26 of the syringe barrel 12 through open rear end 20. The assembly can then be packaged for later use. When assembled as such, fluid communication is generally established throughout the length of the assembled arterial blood collection syringe assembly 10. Specifically, fluid communication is provided through front opening 32 at the front end of syringe barrel 12 (and likewise through needle cannula 44 attached thereto), into the internal space 26, and more particularly the cavity 82, in the syringe barrel 12, through the plurality of vents 62 and the porous filter member 66, through the interior lumen 72 of the plunger rod 58 and out the opened rear end 69 of the plunger rod 58.

In use, the syringe assembly 10 can be used to either passively or actively collect a blood sample from a patient. More particularly, the present invention can be used to collect blood passively by removing the syringe assembly from the packaging and drawing the plunger rod 58 rearwardly relative to the syringe barrel 12 so that a cavity 82 is formed within the syringe barrel 12 (as shown in FIGS. 1 and 2A) that equals the volume of the sample to be collected from a patient. A suitable arterial access device such as needle assembly 38 is connected by interfitting female luer taper 50 over male luer taper 34 and threading luer flanges 52 within the internal threads within luer lock 36 at the front end 22 of the syringe barrel 12. The needle cannula 44 can then be positioned within a vessel of a patient for sample collection.

Upon entry of the needle cannula 44 into the patient's blood vessel, in particular an artery, collection of the blood sample into the cavity 82 within the syringe barrel 12 is immediately facilitated passively by the blood pressure of the patient. In particular, the air within the cavity 82 of the syringe barrel 12 is displaced through the plurality of vents 62 and the porous filter member 66 into the interior lumen 72 of the plunger rod 58 as the blood enters the cavity 82 of the syringe barrel 12.

More particularly, the blood within the patient's artery is pumping at physiological pressure, which is greater than normal atmospheric or ambient pressure. Since the cavity 82 of collection assembly 10 is vented to the external environment through the plurality of vents 62, the air pressure within cavity 82 is at ambient pressure. When the blood within the patient's artery is in fluid contact with the cavity 82, the higher pressure of the patient's artery forces the blood into the lower ambient pressure cavity 82. As such, the blood transfer occurs based on the patient's blood pressure.

During such transfer of blood into the cavity 82, it is necessary to displace the air within the cavity 82 in order to prevent the pressure therein from building to a pressure which would be above the blood pressure and therefore prevent further blood flow into cavity 82. Accordingly, during such blood flow, the air, and any other gases present within cavity 82, must be displaced from within cavity 82. This displacement occurs by venting such air from within cavity 82 through the plurality of vents 62, through the porous filter member 66, through the interior lumen 72 and out through closed rear end 69 of plunger rod 58.

As the cavity 82 of the syringe barrel 12 is gradually filled by the blood sample being collected and the air within the cavity 82 is displaced, the blood sample will eventually contact the conically profiled front end 90 of the plunger rod 58 or, in an alternative embodiment, the flat profiled front end of the plunger rod. The plurality of vents 62 are designed in close proximity to the internal surface 28 of the syringe barrel 12 to ensure that all air is expelled from the cavity 82 before the porous filter member 66 becomes sealed. Accordingly, in any manner that the syringe assembly 10 is held, one of the plurality of vents 62 will always be positioned at a higher position within the syringe barrel 12. This arrangement is further facilitated by positioning the sealing ring 80 spaced from the front end, such that vents 62 can be located directly adjacent the internal surface 28 of syringe barrel 12 when plunger rod 58 is assembled therewith, either adjacent the front end 90 or spaced from the front end 90 (such as vents 62a in FIG. 1). Due to the inherently higher surface tension of the blood sample as compared to the air, any air that is trapped within the cavity 82 of the syringe barrel 12 will rise to the uppermost point of the cavity 82 and be displaced out of the cavity 82 before blood within the cavity 82 reaches and flows through the highest vent of the plurality of vents 62 and, ultimately, contacts the porous filter member 66.

During sampling, the blood will rise within the cavity 82 until it is full, at which point the blood will contact all of the vents 62 and therefore the entire vented surface of the porous filter member 66. Such contact will cause the porous filter member 66 to become gas impermeable, thereby preventing any further blood to enter cavity 82 since no further air can be displaced therefrom. Also, such feature serves to protect the blood sample within the cavity 12 when a two-way filter is used, since no further air will be able to enter into the cavity 12 through the now-sealed filter member 62. Once the self-sealing porous filter member 66 is sealed, an aseptic sample is present in the cavity 82 of the syringe barrel 12 that can be used for analysis of the blood collected from the patient.

Alternatively, the present invention can be used actively to collect blood from a patient by aspiration like a traditional blood sampling hypodermic syringe. In such a procedure, the plunger rod 58 is be positioned in the forwardmost position relative to the syringe barrel 12. The operator of the syringe assembly 10 must then place a thumb over the hole at the open rear end 69 of the plunger rod 58 to seal the opening to the passage of air. While maintaining a seal on the opened rear end 69 of the plunger rod 58, the operator then draws the plunger rod 58 rearwardly relative to the syringe barrel 12 thereby creating a vacuum within the cavity 82 to aspirate a sample of blood from a patient. A cavity 82 is formed within the syringe barrel 12 as the plunger rod 58 is moved rearwardly and then held in a position that will create a cavity 82 within the syringe barrel 12 that equals the desired volume of the sample to be collected from a patient. As previously discussed, the blood sample will enter the cavity 82 of the syringe barrel 12 through the needle cannula 44. As the blood contacts the porous filter member 66, the self-activating seal will form, thereby sealing an aseptic blood sample in the cavity 82 for analysis.

The present invention provides an arterial blood gas syringe which is inexpensive to manufacture and easy to assemble. By constructing the plunger rod out of a one-piece assembly with the vents integrally formed therein, the need for a separate elastomeric plunger sealing tip is eliminated. As such, manufacturing and assembly are simplified. By providing sealing rings about the exterior surface of the plunger rod, and in particular integrally formed therewith, an effective seal can be maintained without the need for the elastomeric plunger sealing tip. By eliminating the elastomeric plunger sealing tip, cost savings are achieved, and the plunger mechanism can slide more freely within the syringe barrel, eliminating the need for separate silicone lubricants which can contaminate the sample contained therein.

While the present invention is satisfied by embodiments in many different forms, there is shown in the drawings and described herein in detail the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed is:

1. A plunger rod assembly adapted for slidable communication within a syringe barrel, the plunger rod assembly comprising:
    an elongated, hollow cylindrical rod comprising a rigid tubular wall defining an internal opening and extending between an open rear end and a monolithic, integrally formed closed front end, the rod including a plurality of vents extending through the rigid tubular wall adjacent the front end of the rod and in fluid communication with the internal lumen, the rod further including at least one sealing ring extending circumferentially about an external surface thereof; and
    a porous filter member maintained within the internal lumen at the front end of the rod and contiguous to the plurality of vents, the porous filter member adapted to filter fluid passing between the plurality of vents and the internal lumen of the rod.

2. The plunger rod assembly of claim 1, wherein the closed front end of the rod includes a circular cross-section and the plurality of vents extend through the rigid tubular wall at a location axially spaced from the closed front end of the rod.

3. The plunger rod assembly of claim 2, wherein the porous filter member contacts an interior surface of the closed front end within the internal lumen such that the plurality of vents are contiguous to the porous filter member at a location spaced from a front surface of the porous filter member.

4. The plunger rod assembly of claim 1, wherein the porous filter member contacts an interior surface of the closed front end within the internal lumen such that the plurality of vents are contiguous to the porous filter member.

5. The plunger rod assembly of claim 4, wherein the plurality of vents are contiguous to the porous filter member at a location contacting at least a portion of a front surface of the porous filter member.

6. The plunger rod assembly of claim 1, wherein the plurality of vents are equally radially spaced about a circumference of the rigid tubular wall.

7. The plunger rod assembly of claim 1, wherein the plurality of vents extend through the rigid tubular wall at an intersection of the closed front end with the rigid tubular wall, thereby forming the plurality of vents about the perimeter of the closed front end.

8. The plunger rod assembly of claim 1, wherein the porous filter comprises a matrix which is pervious to air, and which is adapted to be impervious to air and blood upon contact with a blood sample.

9. The plunger rod assembly of claim 1, wherein the at least one sealing ring is integrally formed with the plunger rod.

10. The plunger rod assembly of claim 1, wherein the at least one sealing ring comprises an elastomeric o-ring affixed to an external surface of the rod.

11. The plunger rod assembly of claim 1, further comprising a pair of sealing rings extending circumferentially about the external surface of the rod and axially spaced from each other.

12. The plunger rod assembly of claim 1, wherein the rod includes a flange extending about a perimeter of the rear end of the plunger rod.

13. The plunger rod assembly of claim 1, wherein the front end of the plunger rod is tapered having a conical profile.

14. A syringe assembly comprising:
    a syringe barrel having an internal chamber extending between an open rear end and a closed front end having an opening extending therethrough;
    an elongated, hollow cylindrical plunger rod extending within the open rear end of the syringe barrel and adapted for slidable communication within the internal chamber of the syringe barrel, the plunger rod comprising a rigid tubular wall defining an internal opening and extending between an open rear end and a monolithic, integrally formed closed front end, the plunger rod including a plurality of vents extending through the rigid tubular wall adjacent the front end of the plunger rod and in fluid communication with the internal lumen, and at least one sealing ring extending circumferentially about an external surface thereof and in sliding contact with an inner surface of the syringe barrel, and
    a porous filter member maintained within the internal lumen of the plunger rod at the front end of the body and contiguous to the plurality of vents,
    wherein the porous filter member is pervious to air and impervious to liquid passing from the internal chamber of the syringe barrel through the vents and into the internal lumen of the plunger body.

15. The syringe assembly of claim 14, wherein the closed front end of the plunger rod includes a circular cross-section and the plurality of vents extend through the rigid tubular wall at a location axially spaced from the closed front end of the plunger rod.

16. The syringe assembly of claim 15, wherein the porous filter member contacts an interior surface of the closed front end of the plunger rod within the internal lumen such that the plurality of vents are contiguous to the porous filter member at a location spaced from a front surface of the porous filter member.

17. The syringe assembly of claim 14, wherein the porous filter member contacts an interior surface of the closed front end within the internal lumen such that the plurality of vents are contiguous to the porous filter member.

18. The syringe assembly of claim 17, wherein the plurality of vents are contiguous to the porous filter member at a location contacting at least a portion of a front surface of the porous filter member.

19. The syringe assembly of claim 14, wherein the plurality of vents extend through the rigid tubular wall at an intersection of the closed front end with the rigid tubular wall, thereby forming the plurality of vents about the perimeter of the closed front end of the plunger rod.

20. The syringe assembly of claim 14, wherein the at least one sealing ring is integrally formed with the plunger rod.

21. The syringe assembly of claim 14, wherein the at least one sealing ring comprises an elastomeric o-ring affixed to an external surface of the plunger rod.

22. The syringe assembly of claim 14, further comprising a pair of sealing rings extending circumferentially about the external surface of the plunger rod and axially spaced from each other, each of the pair of sealing rings in sliding contact with an inner surface of the syringe barrel.

23. The syringe assembly of claim 14, wherein the syringe barrel includes a flange extending about a perimeter of the opened rear end thereof, and the plunger rod includes a flange extending about a perimeter of the opened rear end thereof.

24. The syringe assembly of claim 14, wherein the front end of the syringe barrel includes structure for connecting the syringe assembly with a medical device.

* * * * *